United States Patent [19]

Hempel et al.

[11] 4,332,763
[45] Jun. 1, 1982

[54] METHOD OF MAKING A COSMETIC SUBSTANCE

[75] Inventors: Matthias Hempel, Eckental; Werner Brüchert, Nuremberg, both of Fed. Rep. of Germany

[73] Assignee: Schwan-Stabilo Schwanhausser GmbH & Co., Nuremberg, Fed. Rep. of Germany

[21] Appl. No.: 154,932

[22] Filed: May 30, 1980

[30] Foreign Application Priority Data

Jun. 7, 1979 [DE] Fed. Rep. of Germany ....... 2923080

[51] Int. Cl.³ ............................................... A61K 7/02
[52] U.S. Cl. ................... 264/176 R; 264/234; 264/320; 264/323; 264/330; 424/63; 424/DIG. 5
[58] Field of Search ................... 264/176 R, 330, 320, 264/323, 234–235; 424/63, DIG. 5

[56] References Cited

U.S. PATENT DOCUMENTS

| | | | |
|---|---|---|---|
| 1,312,424 | 8/1919 | Richardson | 264/176 R |
| 2,034,697 | 3/1936 | Factor | 424/63 |
| 3,479,429 | 11/1969 | Morshauser et al. | 264/75 |
| 3,800,034 | 3/1974 | Kircher et al. | 424/63 |
| 3,846,556 | 11/1974 | Handjani et al. | 424/63 |

FOREIGN PATENT DOCUMENTS 2845861 10/1977 Fed. Rep. of Germany .

*Primary Examiner*—Jeffery R. Thurlow

[57] ABSTRACT

The invention makes available a cosmetic product in the form of a solid body, preferably a stick, which can be used as a cream by reason of its composition. The product is produced from a mixture of fatty substances, emulsifiers and water-soluble binders to which so much water is added that a mass of a mouldable consistency is obtained. By way of cold deformation, moulded pieces, preferably in stick form, are made therefrom and from these the water is subsequently extracted so that a solid structure is obtained.

4 Claims, No Drawings

METHOD OF MAKING A COSMETIC SUBSTANCE

The invention relates to a method of making a cosmetic substance for the care of the skin and/or for decorative purposes on the basis of fatty substances, emulsifiers, water-soluble binders and possibly fillers. The composition of such a substance corresponds to that of creams which find many uses in cosmetics. A particular composition will depend on its intended purpose. This applies above all to the nature and amount of the active ingredient. A feature characteristic of all creams is the incorporation of a comparatively large proportion of water—in the case of oil in water emulsions up to 70% by weight—by emulsification of the fatty substances contained in the creams. The creams in this way obtain their typical (cream or salve-like) consistency which is important not only for putting them into tubes or jars but also for their manipulation when applying to the skin. The consumer is used to taking the creams from the container with the fingers and then applying it to the parts of the body to be treated. When withdrawing the cream in this manner, the unused cream remaining in the container necessarily also comes into contact with the fingers in a manner such that it is most likely for the contents to become contaminated with micro-organisms which are detrimental to health and/or stability during storage. The conditions for such contamination of the creams are particularly favourable because of their high moisture content. It is the object of the present invention to overcome the resultant hygienic problems.

DE-OS No. 28 45 861 discloses a deodorant stick which feels like a cream on the skin and from which layers can be applied to the skin when the stick is brought into contact therewith by reason of the emulsifier content of the stick. The structure of this stick is in the form of a solidified gel formed on a soap basis and in which an aqueous dispersion of bicarbonate is incorporated as the deodorant active ingredient. The production of this known stick is effected in that the substance of the stick is transformed to a pourable condition by heating and the mass is then poured into moulds and cooled to room temperature. Gelling takes place on cooling, whereby a stable moulded body is obtained. There is no extraction of moisture in the production of the known stick, which therefore likewise makes contamination possible. Another disadvantage is that processing of the stick substance by means of a casting method does not permit the incorporation of comparatively large amounts of solid substances (e.g. of more than 35% by weight). However, by reason of special applications, such a high content of solids is often desirable in a cosmetic substance.

The invention is based on the object of providing a cosmetic product which, by reason of its composition, offers the same possibilities as conventional creams with a comparatively high moisture content and correspondingly soft consistency but which, in comparison therewith, permits manipulation that is unobjectionable from a hygienic point of view. It is believed that this object is in itself novel and, in achieving it, the applicants have recognised that the product must on the one hand have a sufficient solidity to enable it to be brought into a stick form but on the other hand the mass brought into stick form must be applicable to the skin in the same way as a conventional cream.

With a view to achieving the aforementioned object, the invention suggests that a mass of mouldable consistency is prepared from the aforementioned components with the required amount of water and moulded pieces, preferably in stick form, are made from said mass by cold deformation, water being subsequently extracted from said pieces to an extent such that a solid structure is obtained. The said components may in addition to the aforementioned fatty substances, emulsifiers, water-soluble binders and fillers also include dyes as well as active ingredients having a cosmetic and/or medicinal effect. Where, in conjunction with the method according to the invention, reference is made to the fact that the water is extracted from the moulded pieces to an extent such that a 'solid structure' is obtained, this is intended to mean a structure which can no longer be deformed without being destroyed. Extraction of the water is preferably by drying in air. The residual water content in the moulded pieces will often be between 2 and 5% by weight.

By means of the invention, one obtains a cosmetic mass which can be regarded as an instant cream which, compared with conventional creams, is characterised particularly by its absence of water or a comparatively extremely low water content. The danger of contamination in the case of such a mass is considerably lower.

The dry cream in the form of a compact piece in accordance with the invention is applied to the pre-moistened skin. By reason of the emulsifier contained in the dry cream, emulsification of the fat in the cream then takes place on the skin whereby the cream at the same time becomes smearable or spreadable and a layer of it can be applied to the skin.

To perform the method of the invention, suitable fatty substances as a basis for the cream are all substances conventionally used in the cosmetic industry, namely fats, oils and waxes, saturated and unsaturated fatty acids and their esters with higher alcohols or their glycerides in an oily, salve-like as well as solid consistency.

Suitable emulsifiers are practically all substances of this kind which are physiologically unobjectionable, e.g. fatty acid sorbitane esters, polyethylene oxide and its numerous derivatives as well as ionogenically composed emulsifiers.

Suitable fillers are kaolin, talcum, calcium carbonate, metal soaps or mica.

To bind the solid substances contained in the dried stick, including any dyes in soluble or pigment form, it is very advantageous for the purpose of achieving an adequate solidity for the compact pieces to incorporate a water-soluble binder such as polyvinyl pyrrolidone, carboxymethyl cellulose, dextrine, tragacanth etc.

When performing the method of the invention, one generally proceeds by first kneading the individual components together with the binder and an amount of water required for dissolving the binder—about 20 to 30% of the entire mass. The resultant kneadable mass is then brought into cylindrical moulded pieces by cold deformation, preferably by extrusion, and the water is then extracted from them in known manner (air drying, possibly at temperatures above room temperature). By reason of the adhering effect of the water-soluble binders worked into the resultant moulded pieces, the latter have a high mechanical strength and can therefore be cemented in wood to form sharpenable sticks or pencils and can also be introduced in sleeves in chalk form. The content of such binders together with the emulsifier proportion in the substance of the stick enable the (instant) cream to become detached from the applying surface of the stick in conjunction with the moisture on the skin. In other words, it need not be rubbed off mechanically. In this way, the properties of using the stick of cream produced according to the invention approximate to those of conventional cream.

A few examples will now be given of the composition of masses which can be processed by the method of the invention, it being understood that water still has to be added in an amount required to make the masses deformable by way of cold deformation. After moulding, the mass of the stick has so much water withdrawn from it that an adequately solid structure is obtained.

EXAMPLE 1

The following composition is intended for a cosmetic substance having a skin-care effect.

| | | Proportion by Weight |
|---|---|---|
| Dyes: | TiO₂ | 7 |
| | Iron oxide dyes | 2 |
| Emulsifiers: | Condensation compound of cetyl and stearyl alcohol with 20 mol ethylene oxide | 5 |
| | Sorbitane stearate | 1 |
| Cream Basis: | Vaseline | 3.5 |
| | Arachidylpropionate | 2.5 |
| | di-n-butyl adipate | 2 |
| Active Ingredient: | Mixture of fatty acid esters from the PCL group by Messrs. DRAGOCO | 2 |
| | Wheat germ - glyceride | 2.5 |
| | Sodium salt of a polyhydroxy carboxylic acid | 1 |
| | Quaternium 23* | 0.5 |
| | Glycerine | 1 |
| Binder: | Polyvinyl pyrrolidone | 5.5 |
| Fillers: | Kaolin | 25 |
| | Talcum | 25 |
| | Mica | 14.5 |
| | | 100 |

*Quaternary ammonium polymer obtained by the reaction of dimethyl-sulphate with a mixed polymer of vinyl pyrrolidone and dimethylamino ethylmethacrylate

EXAMPLE 2

The following composition is suitable for a cosmetic substance having a skin-care as well as disinfecting property.

| | | Proportion by Weight |
|---|---|---|
| Dyes: | Pearl pigments | 4 |
| | TiO₂ | 1.5 |
| | Iron oxide pigments | 2.5 |
| Emulsifiers: | Mixture of long-chained alcohols with non-ionogenic emulsifier | 5 |
| | Polysorbate 20 (20 mol ethylene oxide) | 1 |
| Cream Basis: | Vaseline | 4 |
| | Dioctyladipate, octylstearate, octylpalmitate | 2.5 |

| | | Proportion by Weight |
|---|---|---|
| | n-butylstearate | 0.5 |
| Active Ingredients: | PCL W/OE* | 2 |
| | Wheat germ glycerides | 2.5 |
| | Sodium salt of a polyhydroxy carboxylic acid | 1 |
| | Quaternium 23 | 1 |
| | Glycerine | 1.5 |
| | Alkyldimethyl benzyl ammonium saccharinate | 2.5 |
| Binder: | Carboxymethyl cellulose | 5 |
| Fillers: | Kaolin | 24.5 |
| | Talcum | 24.5 |
| | Mica | 14.5 |
| | | 100 |

*Mixture of a purified oleic acid ester and a high-grade lanolin-alcohol fraction with 36% of a mixture of alkyl-interlinked and long-chained fatty acid esters produced by Messrs. DRAGOCO.

EXAMPLE 3

The following composition is intended for a substance having a caring and healing effect.

| | | Proportion by Weight |
|---|---|---|
| Dyes: | Pearl pigments | 8 |
| | Iron oxide pigments | 2.5 |
| Emulsifiers: | Glycerine mono-di-esters of palmitic/stearic acid | 5 |
| | N-β-hydroxyethyl-N-β-carboxyethyl-fatty acid amido ethyl amine, Na-salt | 1.5 |
| Cream Basis: | Vaseline | 4 |
| | Arachidylpropionate | 2.5 |
| | n-butylstearate | 0.5 |
| Active Ingredients: | Sulfosuccinate derivative | 1.5 |
| | Na salt of a polyhydroxy carboxylic acid | 1.5 |
| | Quaternium 23 | 1 |
| | Calendula oil | 1 |
| | Allantoin | 0.5 |
| | Camomile extract | 0.5 |
| | Biobranil (DRAGOCO) | 1.5 |
| Binder: | Dextrine | 5 |
| Fillers: | Kaolin | 24 |
| | Talcum | 24 |
| | Mica | 15.5 |
| | | 100 |

We claim:

1. A method for the production of a cosmetic stick comprising cold deformation molding a mixture comprising a fatty substance for the creation of a cream-like layer for application to the skin, a water soluble binding agent and an agent which emulsifies on the skin upon the addition of water, and thereafter removing water from the said molded mixture to such an extent that the stick so formed by the said cold deformation hardens into a solid structure.

2. The method of claim 1, wherein sufficient water is removed to result in a residual water content of from about 2 to 5 percent by weight.

3. The method of claim 1 or 2 wherein the mixture contains a filler.

4. The method of claim 1, wherein the cold deformation is effected by extrusion.

* * * * *